United States Patent [19]
Wilson et al.

[11] 3,958,030
[45] May 18, 1976

[54] FLAVORING COMPOSITIONS AND PROCESSES UTILIZING SIX MEMBERED HETERO-CYCLIC-POLY-S-COMPOUNDS

[75] Inventors: Richard Arnold Wilson, Westfield; Ira Katz, West Long Branch; Manfred H. Vock, Locust, all of N.J.; Edward J. Shuster, Brooklyn, N.Y.

[73] Assignee: International Flavors & Fragrances Inc., New York, N.Y.

[22] Filed: Oct. 23, 1975

[21] Appl. No.: 625,199

Related U.S. Application Data

[60] Continuation-in-part of Ser. No. 560,717, March 21, 1975, which is a division of Ser. No. 166,683, July 28, 1971, abandoned.

[52] U.S. Cl. ............................................. 426/535
[51] Int. Cl.² ........................................ A23L 1/235
[58] Field of Search ................................... 426/535

[56] References Cited
UNITED STATES PATENTS
2,594,379   4/1952   Bareh............................ 426/535 X Primary Examiner—Joseph M. Golian
Attorney, Agent, or Firm—Arthur L. Liberman; Harold Haidt

[57] ABSTRACT

A small but effective amount of a compound represented by the formula:

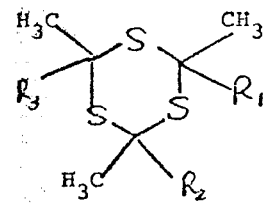

wherein $R_1$, $R_2$, and $R_3$ are the same and represent hydrogen or methyl, is used to alter, modify or enhance the flavor and aroma characteristics of a foodstuff, chewing gum or medicinal product.

3 Claims, 8 Drawing Figures

EXAMPLE I

GLC SPECTRUM:
PEAKS 147 - 162

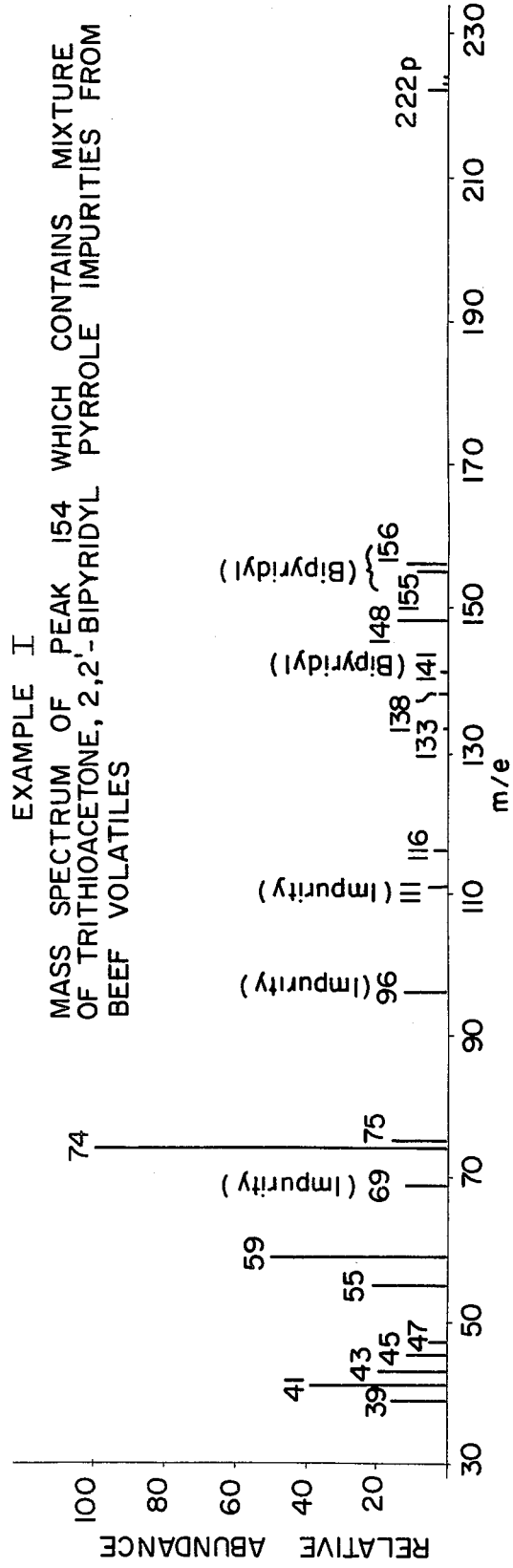
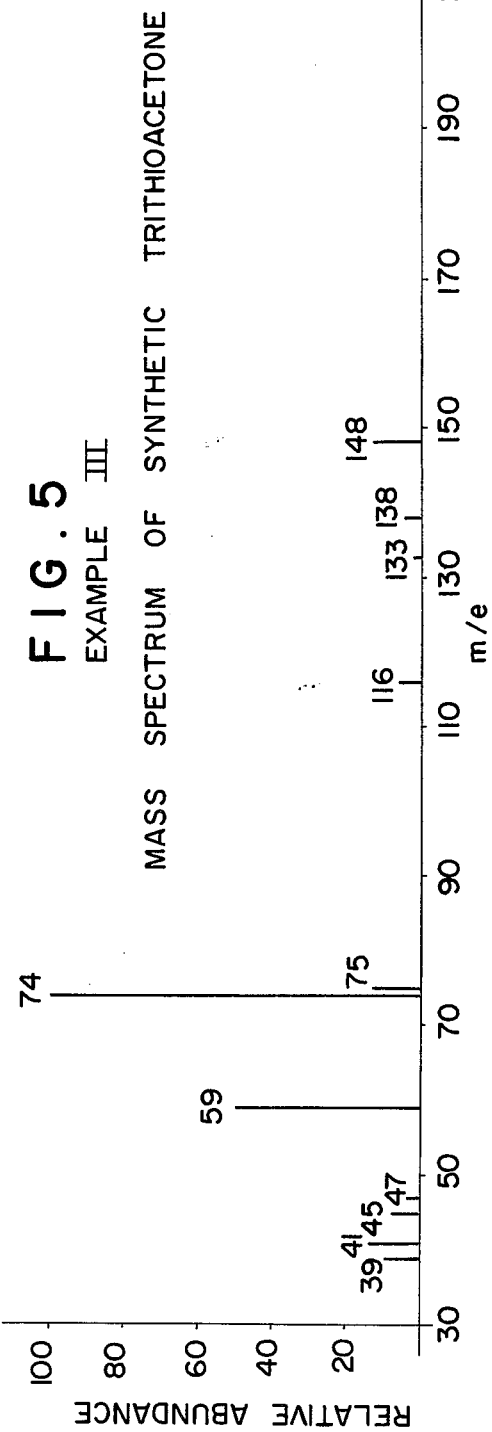

EXAMPLE II

GLC SPECTRUM
PEAKS 72-92

EXAMPLE II
MASS SPECTRUM OF PEAK 81 WHICH CONTAINS TRITHIOACETALDEHYDE FROM BEEF VOLATILES

EXAMPLE IV
MASS SPECTRUM OF SYNTHETIC TRITHIOACETALDEHYDE

EXAMPLE III
NMR SPECTRUM OF SYNTHETIC TRITHIOACETONE
1000 Hz SWEEP WIDTH

FLAVORING COMPOSITIONS AND PROCESSES UTILIZING SIX MEMBERED HETERO-CYCLIC-POLY-S-COMPOUNDS

This application is a continuation-in-part of U.S. application for Letters Patent Ser. No. 560,717, field on Mar. 21, 1975, which in turn, is a divisional application of Ser. No. 166,683, filed July 28, 1971 and now abandoned.

THE INVENTION

This invention has to do with the use of certain trithianes to alter, modify or enhance the flavor and aroma of consumable materials; foodstuffs, chewing gums, and medicinal products.

The term "foodstuff" as used herein includes both solid and liquid ingestible materials for man or animals which materials usually do, but need not, have nutritional value. Thus, foodstuffs include meats, gravies, soups, convenience foods, malt and other alcoholic or non-alcoholic beverages, nut butter such as peanut butter and other spreads, seafoods including fish, crustaceans, mollusks and the like, candies, breakfast foods, baked goods, vegetables, cereals, soft drinks, snack foods, pet foods such as dog and cat foods, other veterinary products, and the like.

The term "chewing gum" is intended to mean a composition which comprises a substantially water-isoluble, chewable plastic gum base such as chicle, or substitutes therefor, including jelutong, guttakay, rubber or certain comestible nature or synthetic resins or waxes. Incorporated with the gum base in admixture therewith may be plasticizers or softening agents, e.g., glycerine; and a flavoring composition which incorporates one or more of the trithianes of our invention, and in addition, sweetening agents which may be sugars, including sucrose or dextrose and/or artificial sweeteners such as cyclamates or saccharin. Other optional ingredients may also be present.

The term "medicinal product" includes both solids and liquids which are ingestible non-toxic materials which have medicinal value such as cough syrups, cough drops, aspirin and chewable medicinal tablets.

The terms "alter" and "modify" (in their application to foodstuffs) in its various forms will be understood herein to mean the supplying or imparting of a flavor character or note to an otherwise bland, relatively tasteless substance, or augmenting an existing flavor characteristic where the natural flavor is deficient in some regard, or supplementing the existing flavor impression to modify the organoleptic character.

The term "enhance" is used herein to mean the intensification of a flavor or aroma characteristic or note without the modification of the quality thereof. Thus, "enhancement" of a flavor or aroma means that the enhancement agent does not add any additional flavor note.

There is a continuing search for compositions which can vary, fortify, modify, enhance or otherwise improve (i.e. alter) the flavor and aroma of a foodstuff. To be fully satisfactory, such compositions should be stable, non-toxic, and blendable with other ingredients to provide their own unique flavor and aroma nuance without detracting from the co-ingredients. Preferably, such compositions should be naturally occurring or present in natural foodstuffs (although unrecognized as flavor components thereof) so that their ingestible safety can be readily recognized. Additionally, these materials should be capable of being synthesized in a simple and economic manner.

Various heterocyclic poly-S compounds have been shown in the literature to have flavor implications. For example, in U.S. Pat. No. 3,503,758 to Wada et al., pentathiepane, tetrathiane and tetrathiepane are said to have a flavor and aroma; and Chang in *Chemistry and Industry*, 1639, Nov. 23, 1968, reports 3,5-dimethyl-1,2,4-trithiolane as present in the volatiles of boiled beef. Other investigators have commented that poly alkyl trithianes are odorless or have an intensely putrid odor. See Barch, U.S. Pat. No. 2,594,379 and Breslau and Skolnik, "Heterocyclic Compounds", p. 726, *Interscience* (1966). Pippen in *Journal of Food Science*, 34, p. 443–446 (1969) speculated that $H_2S$ reacted with a carbonyl compound in chicken fat and postulated that 2,4,6-trimethyl-S-trithiane could be one of the products formed.

Corey, et al., U.S. Pat. No. 3,492,313 discloses the concept of using various salts of 1,3,5-trithianes as precursors of various aldehydes and ketones which are, in turn, useful as flavoring agents (Col. 1, lines 38–40). The reaction sequence of Corey, et al.:

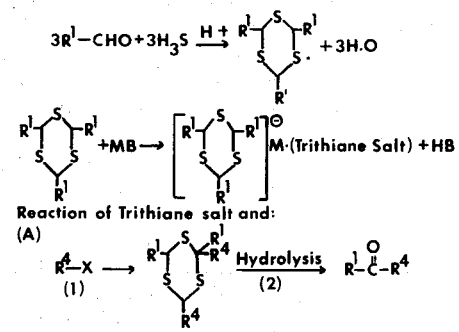

$M = Li, K, Na$; $B = NH_2$, H, lower alkyl, lower alkoxy, phenyl; $X =$ chlorine, bromine, iodine, phenylsulfonate and alkyl-phenylsulfonate; $R_1$, $R_8$, $R_9$, $R_{11}$, $R_{12}$, $R_{13}$, $R_{14} =$ hydrogen, alkyl, phenyl, alkylphenyl and phenyl alkyl; and $R_4 =$ alkyl, phenylalkyl and arylalkyl, embodies a concept different in kind from that of the instant invention.

It has now been found that the flavor of a food-stuff can be altered by adding thereto a small but effective amount of at least one heterocyclic poly-S compound having the formula:

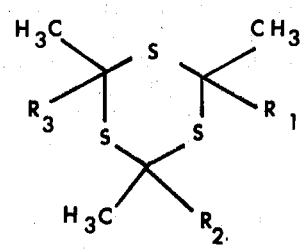

wherein $R_1$, $R_2$ and $R_3$ are the same and are either hydrogen or methyl. The invention also contemplates fruit-type flavoring compositions containing such heterocyclic poly-S compounds.

The trithianes have a sweet nutty aroma and taste and are suitable for fruit (gooseberry, black currant, grape, raspberry) nut and meat flavors.

The structural formulae given herein contemplate and include cis- and trans- and other conformational isomers.

The trithianes of our invention can be prepared in a known manner such as that described by Campaigne, Chem. Reviews, 39, No. 1, pp. 1–77, August 1946. Applicants have also found that the compounds: 2,4,6-trimethyldihydro-1,3,5-dithiazine; 2,4,6-trimethyl-s-trithiane; and 2,2,4,4,6,6-hexamethyl-s-trithiane, are present in the volatiles of beef extract.

When the heterocyclic poly-S compounds according to this invention are used in a flavoring composition, they can be combined with conventional flavoring materials or adjuvants. Such co-ingredients or flavoring adjuvants are well-known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surface active agents, conditioners and flavor intensifiers.

Such conventional flavoring materials include saturated and unsaturated fatty and amino acids, alcohols, including primary and secondary alcohols; esters, carbonyl compounds including ketones and aldehydes; lactones, other cyclic organic materials including benzene derivatives, alicyclics, heterocyclics such as furans, pyridines, pyrazines and the like; sulfur-containing materials including thiols, sulfides, disulfides and the like; proteins; lipids; carbohydrates; so-called flavor potentiators such as monosodium glutamate, guanylates, and inosinates; natural flavoring materials such as cocoa, vanilla and caramel; essential oils and extracts such as anise oil, clove oil and the like; artificial flavoring materials such as vanillin; and the like.

Stabilizers include preservatives such as sodium chloride, and the like; antioxidants such as calcium and sodium ascorbate, ascorbic acid, butylated hydroxyanisole, butylated hydroxytoluene, propyl gallate and the like; sequestrants such as citric acid, EDTA, phosphates, and the like.

Thickeners include carriers, binders, protective colloids, suspending agents, emulsifiers and the like, such as agar-agar, carrageenan, cellulose and cellulose derivatives such as carboxymethyl cellulose and methyl cellulose, natural and synthetic gums such as gum arabic, gum tragacanth and the like, and other proteinaceous materials, lipids, carbohydrates, starches and pectins.

Surface active agents include emulsifying agents such as mono- and/or diglycerides of fatty acids such as caproic acid, caprylic acid, palmitic acid, myristic acid, oleic acid, and the like; lecithin; defoaming and flavor-dispersing agents such as sorbitan monostearate, potassium stearate, hydrogenated tallow alcohol, and the like.

Conditioners include compounds such as bleaching and maturing agents such as benzoyl peroxide, calcium peroxide, hydrogen peroxide and the like; starch modifiers such as peracetic acid, sodium chlorite, sodium hypochlorite, propylene oxide, succinic anhydride and the like; buffers and neutralizing agents such as sodium acetate, sodium diacid phosphate, ammonium bicarbonate, ammonium phosphate, citric acid, lactic acid, vinegar and the like; colorants such as carminic acid, cochineal, turmeric, curcumin, approved food and drug dyes, and the like; firming agents such as aluminum sodium sulfate, calcium chloride and calcium gluconate; texturizers; anti-caking agents such as aluminum calcium sulfate and tribasic calcium phosphate; enzymes; yeast foods such as calcium lactate and calcium sulfate; nutrient supplements such as iron salts, such as ferric phosphate, ferric pyrophosphate, ferrous gluconate and the like, riboflavin, vitamins; zinc sources such as zinc chloride, zinc sulfate, and the like.

The heterocyclic-poly-S-compounds, or the compositions incorporating them, as mentioned above, can be combined with one or more vehicles or carriers for adding them to the particular product. Vehicles can be edible or otherwise suitable materials such as ethyl alcohol, propylene glycol, water, and the like. Carriers include materials such as gum arabic, carrageenan, other gums, and the like. The heterocyclic-poly-S-compounds can be incorporated with the carriers by conventional means such as spray-drying, drum drying, and the like. Such carriers can also include materials for coacervating the heterocyclic-poly-S-compounds (and other flavoring ingredients, as present) to provide encapsulated products. When the carrier is an emulsion, the flavoring composition can also contain emulsifiers such as mono- and diglycerides of fatty acids and the like. With these carriers or vehicles, the desired physical form of the composition can be prepared.

It will be understood by those skilled in the art that the heterocyclic-poly-S-compounds can be added to the materials to be flavored at any convenient point in the production of the finished product. Thus, when they are used to alter or otherwise vary the flavor of a foodstuff, they can be added in the original mixture, dough, emulsion, batter or the like, prior to any cooking or heating operation. Alternatively, they can be added at a later stage of processing if volatilization losses would be excessive during the earlier processing.

The quantity of heterocyclic-poly-S-compounds or mixtures thereof utilized should be sufficient to impart the desired flavor characteristic to the product, but on the other hand, the use of an excessive amount of the heterocyclic-poly-S-compound is not only wasteful and uneconomical but in some instances too large a quantity may unbalance the flavor or other organoleptic property of the product to be consumed. The quantity used will vary depending upon the ultimate foodstuff or other consumable product; the amount and type of flavor initially present in the product; the further process or treatment steps to which the product will be subjected; regional and other preference factors; the type of storage, if any, to which the product will be subjected; and the preconsumption treatment, such as baking, frying, and so on, given to the product by the ultimate consumer.

It is accordingly preferred that the ultimate compositions contain from about 0.02 parts per million (ppm) to about 100 ppm of the heterocyclic-poly-S-compounds. More particularly, in food compositions it is desirable to use from about 0.02 to about 20 ppm and in certain preferred embodiments of the invention, from about 0.1 to about 15 ppm of the heterocyclic-poly-S-compounds are included in the finished product.

The amount of heterocyclic-poly-S-compounds to be utilized in flavoring or flavor-enhancing compositions can be varied over a wide range depending upon a particular quality to be added to the foodstuff, tobacco, or other consumable material. Thus, amounts of one or more heterocyclic-poly-S-compounds according to the present invention from about 0.1 up to 80 or 90% can be incorporated in such compositions. It is generally found to be desirable to include from about 0.5 to about 25% of the heterocyclic-poly-S-compounds in such compositions.

BRIEF DESCRIPTION OF THE DRAWINGS

FIG. 2 is the mass spectrum for GLC peak 154 (m/e vs. relative abundance) of the GLC peaks 147–162 of a beef extract prepared according to Example I.

FIG. 5 is the mass spectrum of trithioacetone, produced according to the synthesis set forth in Example III.

The following examples are given to illustrate embodiments of the invention as it is presently preferred to practice it. It will be understood that these examples are illustrative, and the invention is not to be considered as restricted thereto except as indicated in the appended claims.

EXAMPLE I

40 Pounds of ground round lean beef is slurried in 5 gallons of distilled water and placed in a 20 gallon steam jacketed doubly stirred stainless steel pressure reaction vessel. The vessel is sealed, heated to 182°C and held at this temperature for a period of 15 minutes. The maximum pressure attained is 90 psig. The vessel is cooled by passing water through the jacket. The vessel is then opened and the contents are steam distilled at atmospheric pressure. Two gallons of distillate are recovered. The residue is recharged with two gallons of fresh distilled water and the atmospheric steam distillation operation is repeated. This procedure is repeated four more times so that a total of 12 gallons of steam distillate is obtained. This material is then stored at 5°C in covered buckets until extraction.

Figure 1:
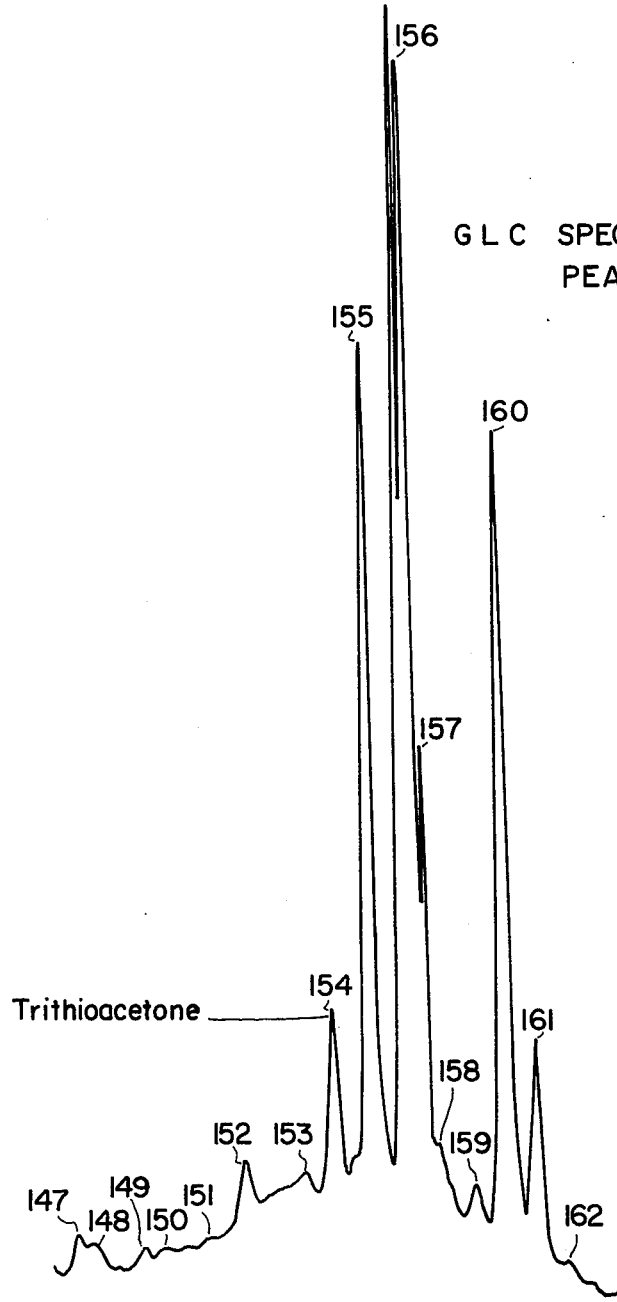
FIG. 1 illustrates the GLC peaks 147–162 of a beef extract prepared according to Example I.

Extraction is performed in a continuous fashion with distilled diethyl ether using approximately 22 liter portions of aqueous distillate. The ether extracts total 2.5 liters. They are combined, dried over anhydrous $Na_2SO_4$ and concentrated in a Kuderna-danish evaporative concentrator to a volume of approximately 5 ml, which concentrate is now subjected to analysis. The extract is subjected to GLC/MS analysis (500 feet × 0.03 inch SF-96 stainless steel capillary) yielding over 200 peaks. GLC peaks 147–162 are set forth in FIG. 1. Peak 154 is analyzed by mass spectral analysis, and its GLC retention index, is measured. The mass spectrum (See FIG. 2) indicates a molecular weight of 222. The isotope ratio 224/222 is measured as approximately 14% which suggest the presence of 3 sulfur atoms in the molecule. The relatively large 148 peak corresponding to M-74 and the base peak of 74 strongly suggest a cyclic, symmetrical trimer the repeating group of which has a molecular weight of 74. This is consistent with a thioacetone trimer which is subsequently synthesized (see Example III). Comparison of its mass spectrum and GLC retention index with those of peak 154 confirm the identification of the latter as trithioacetone (which contains 2 impurities: 2,2'-bipyridyl with peaks at 156/155/141 and an unidentified pyrrole with peaks at 111/96).

EXAMPLE II

40 Pounds of ground lean beef is slurried in 5 gallons of distilled water and placed in a 20 gallon steam jacketed doubly stirred stainless steel pressure reaction vessel. The vessel is sealed, heated to 182°C and held at this temperature for a period of 15 minutes. The maximum pressure attained is 90 psig. The vessel is cooled by passing water through the jacket. The vessel is then opened and the contents are steam distilled at atmospheric pressure. Two gallons of distillate are recovered. The residue is recharged with two gallons of fresh distilled water and the atmospheric steam distillation operation is repeated. This procedure is repeated four more times so that a total of 12 gallons of steam distillate is obtained. This material is then stored at 5°C in covered buckets until extraction.

Figure 3:
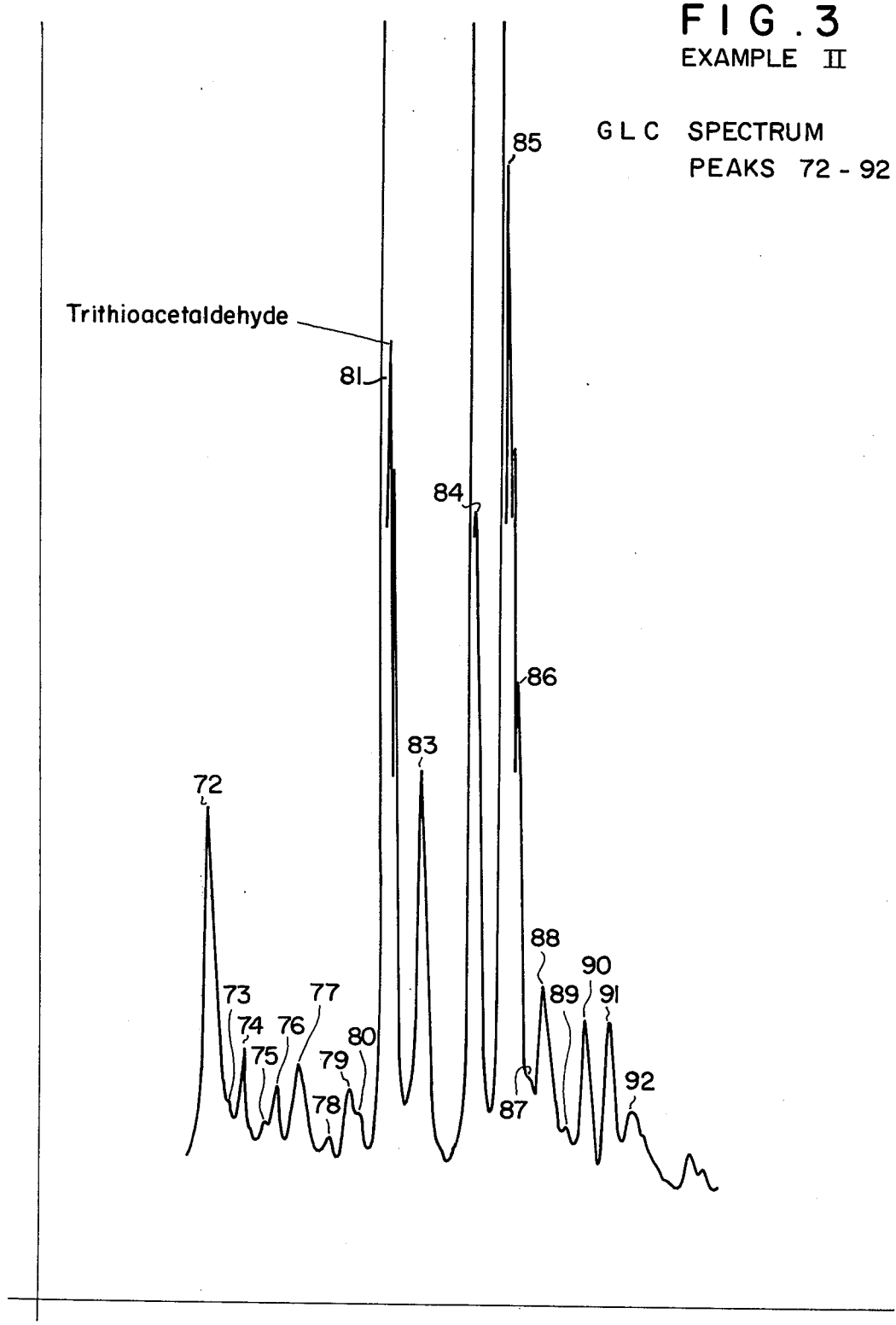
FIG. 3 illustrates the GLC peaks 72–92 of a beef extract prepared according to Example II.
Figure 4:
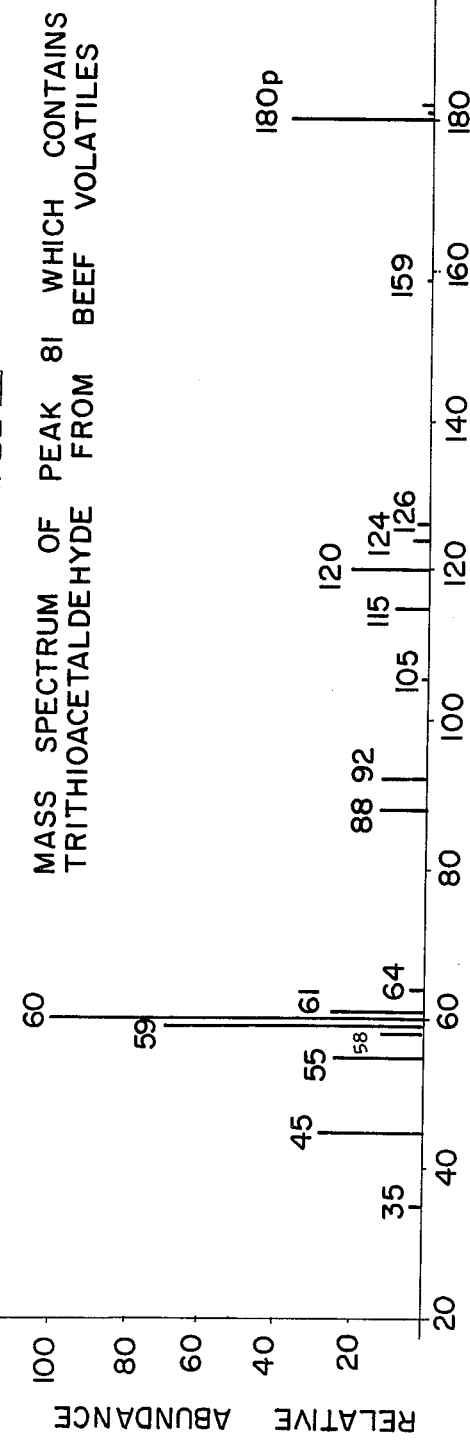
FIG. 4 is the mass spectrum for GLC peak 81 (m/e vs. relative abundance) of the GLC peaks 72–92 of a beef extract prepared according to Example II.

Extraction is performed in a continuous fashion with distilled diethyl ether using approximately 22 liter portions of aqueous distillate. The ether extracts total 2.5 liters. They are combined, dried over anhydrous $Na_2SO_4$ and concentrated in a Kuderna-danish evaporative concentrator to a volume of approximately 5 ml, which concentrate is now subjected to repetitive preparative GLC on a 15 feet × ⅜ inch stainless steel column containing 20% Carbowax 20M on 30/60 mesh Chromasorb W. 9 Area traps are collected and subjected to GLC analysis on a 500 feet × 0.03 inch SF-96 stainless steel capillary. The analysis of trap No. 7 yields over 150 peaks. GLC peaks 72–92 are set forth in FIG. 3. Peak 81 is analyzed by mass spectroscopy and its GLC retention index is measured. The mass spectrum (see FIG. 4) shows a molecular weight of 180. The isotope ratio 182/180 is measured as approximately 14% which suggests that the molecule contains 3 sulfur atoms. The relatively large 120 peak corresponding to M-60 and a base peak of 60 plus the isotope ratios of 122/120 and 62/60 being 8.2% and 4% respectively strongly suggest that the molecule is a cyclic symmetrical trimer the repeating monomer of which has a molecular weight of 60 and contains one S atom. The most obvious compound fitting this description is trithioacetaldehyde which is subsequently synthesized (see Example IV). Comparison of its mass spectrum and GLC retention index with those of peak 81 confirm the identification of the latter as trithioacetaldehyde.

EXAMPLE III

SYNTHESIS OF TRITHIOACETONE

50 Grams of $ZnCl_2$ suspended in 150 ml of acetone is chilled to approximately 0°C in a 500 ml round-bottomed flask equipped with a gas dispersion tube, an immersion thermometer, a mechanical stirring apparatus and a water-cooled reflux condenser the other end of which leads to the hood sink via a rubber hose. The apparatus is placed in a wet ice/salt bath. $H_2S$ is bubbled through the suspension with stirring at a rate sufficient to maintain the temperature below 10°C. Almost immediately the reaction mix turns a pinkish color. Addition of H₂S is maintained for 1 hour. The mixture is then allowed to attain room temperature and stirred at that temperature for an additional one-half hour without further addition of H₂S. The pinkish liquid is decanted off the solid which forms in the bottom of the reaction flask. It is dried over anhydrous Na₂SO₄ and fractionally distilled at 15 mm of Hg. The unreacted acetone distills first and is not collected in the receiver but is stopped in the dry ice/acetone trap. When all the acetone distills over, fraction No. 1 begins to distill between 22.5° and 29°C. It is pinkish-orange in color, very pungent and totals approximately 15 ml, not counting that which is carried over into the dry ice/acetone trap. The temperature then drops to 25°C and the distillation product begins to darken as if it is decomposing. After several minutes during which nothing distills over, a bright red substance begins to distill and is collected between 30° and 112°C. It totals approximately 10 ml not counting that which is not stopped in the receiver and ends up in the dry ice/acetone trap. It has a very mild, slightly oniony odor. This is fraction 2. The distillation is stopped here because the red color is still in the column and the next fraction is colorless. The equipment is cleaned and distillation is recommenced at 15 mm. Fraction 3 is collected between 110° and 113°C. Distillation is stopped when the temperature begins to drop. The following observations are recorded during the collection of fraction 3:

As the distillate progresses up the column it is water white, however, it turns carmine red in the condenser and is collected as such. After storage at −28°C for several days the red color slowly changes to light yellow orange. The vacuum is increased to 2 mm and a fourth fraction is collected at 77°C which comes over royal purple and then turns carmine red after a minute.

Figure 8:
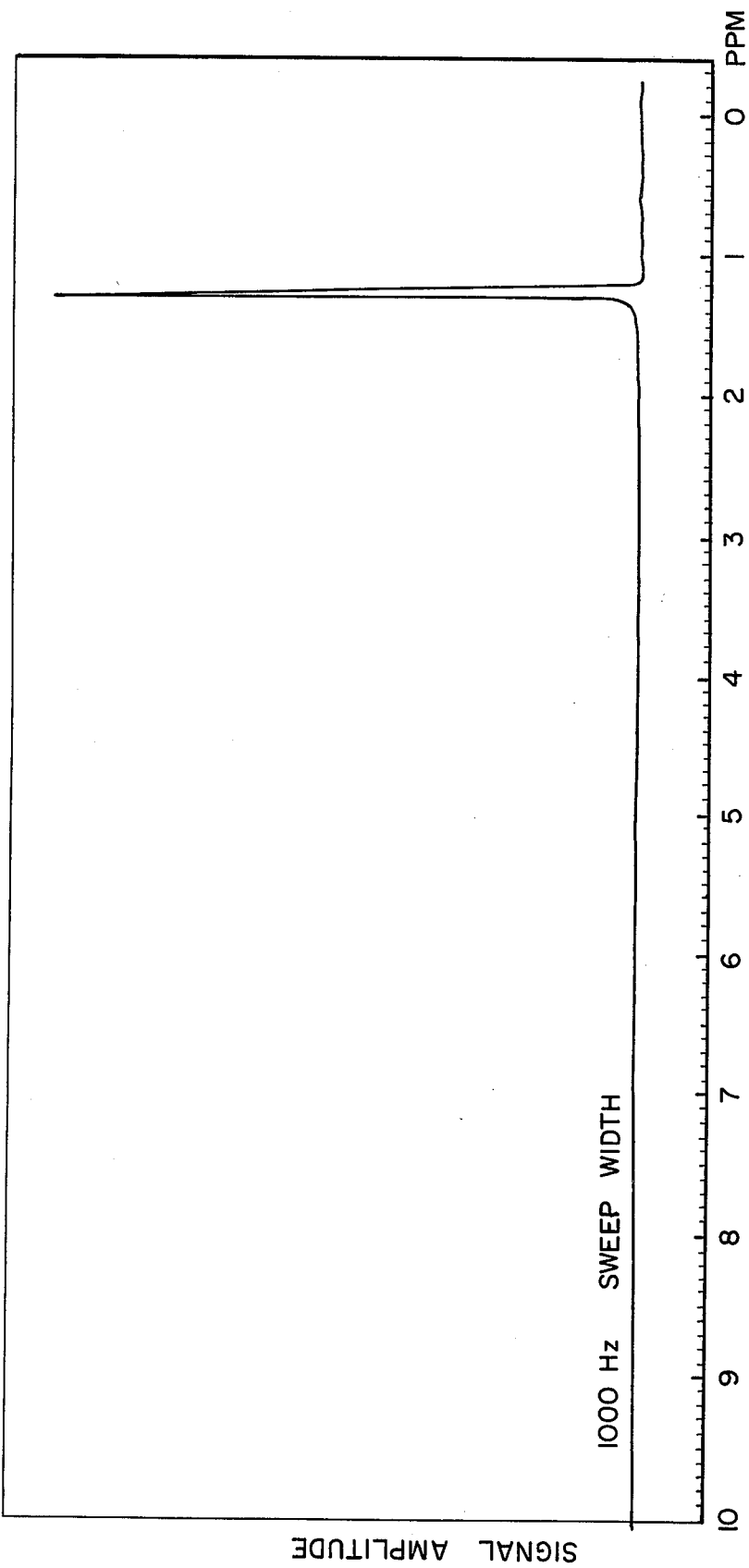
FIG. 8 is the NMR spectrum of trithioacetone produced according to the synthesis set forth in Example III.

Fractions 2 and 3 are analyzed by GLC/MS; each contains three major components which are identified in increasing order of abundance: monothioacetone, 2,2,4,6,6-pentamethyl-1,3-dithi-4-ene; and trithioacetone. The structures of the last two are confirmed by NMR analysis. FIG. 5 is the mass spectrum of synthetic trithioacetone. FIG. 8 is the NMR spectrum of trithioacetone.

Sufficient quantity of trithioacetone is trapped by preparative GLC for flavor evaluation.

Fractions 2 and 3 are combined and redistilled at 0.5 mm Hg.

| Fraction 1- 75°C–81°C | 90.8% pure |
| Fraction 2- 81°C–78°C at 1.5 mm | 98.3% pure |
| Fraction 3- 78.5°C | 99.8% pure |

EXAMPLE IV

SYNTHESIS OF TRITHIOACETALDEHYDE

Into a 2 liter three-necked round-bottomed flask equipped with a mechanical stirring apparatus, a 1 liter addition funnel, an immersion thermometer, a gas-dispersion tube and a dry ice-isopropanal reflux condenser the outlet of which is connected to a series of gas bubbling traps containing alkali solutions and finally leading to the hood sink is placed 132 grams (3 moles) of freshly distilled acetaldehyde. H₂S, from a cylinder, is introduced under low positive pressure below the level of the reaction mix. The gas flow is adjusted to allow minimum escape of gas as evidenced by gas flow through the gas traps. 500 ml of concentrated hydrochloric acid is added via the addition funnel dropwise during a period of approximately one-half hour. After approximately 10 minutes a flocculent white precipitate is observed. At the end of approximately 1 hour the reaction mass thickens so as to preclude stirring and the addition of H₂S and stirring are ceased. As it is not intended to optimize yield, the crystalline material is purified by transferring it onto a large sintered glass filter funnel (this is facilitated by rinsing with small quantitites of acetone) and filtering under water aspirator vacuum. The white solids are recrystallized several times from acetone. After partially drying the crystals on the filter bed for about 2 hours, the crystals are further dried in a vacuum desiccator at room temperature for approximately 1 week until a sharp melting point of 76°–78°C is observed. The yield is 42 grams or 23% of the theoretical yield of 180 grams.

Note: It has been observed [Klinger, Chem. Ber, 9, 1893 (1876); Klinger, Chem. Ber., 10, 1877 (1877); Campaigne, Chem. Rev., 39 (1), 6(1946)] that trithioacetaldehyde can exist in both the cis (beta) and trans (alpha) forms, each exhibiting distinctly different melting points (alpha: 101°C; beta: 125°–126°C). In addition, Drugman and Stockings, Proc. Chem. Soc., 20, 115 (1904) reported a gamma form melting at 76°C which has subsequently been identified as a eutectic mixture consisting of 60% alpha and 40% beta isomers (Rec. des Travaux . . . , 24, 377 (1905); *J. Chem. Soc.*, 1462(1929)). The material isolated in the experiment described above, in addition to exhibiting a melting point in the range assigned to the eutectic, gave an NMR spectrum which could only be interpreted as belonging to a 60/40 mixture of trans/cis isomers (see Campaigne, et al., *J. Org. Chem.*, 27, 135 (1962)).

Figure 6:
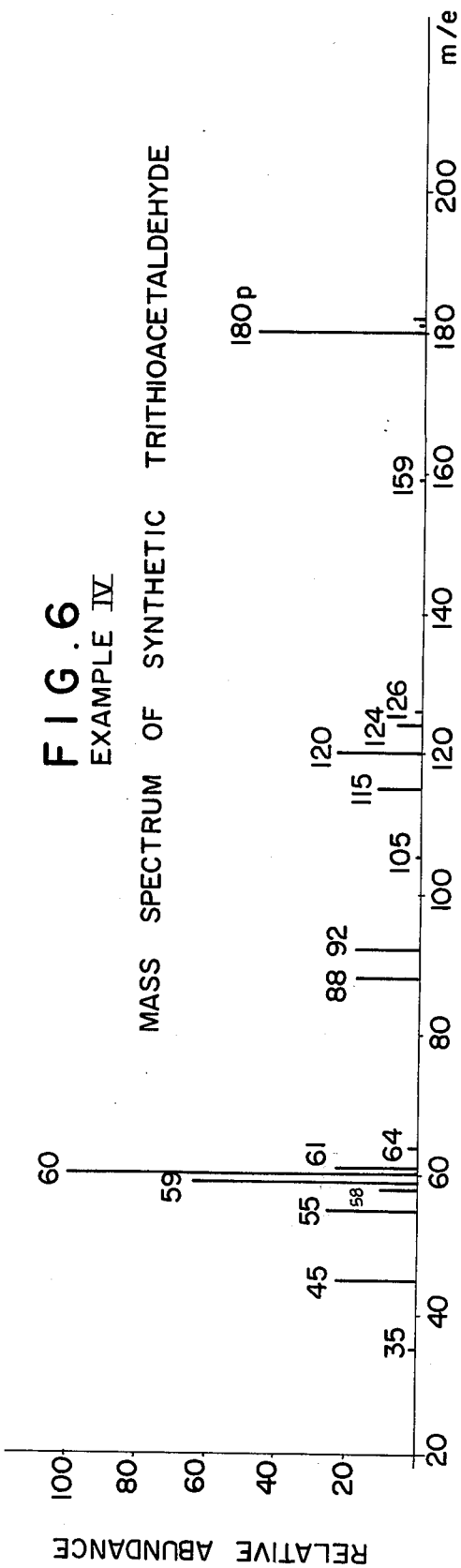
FIG. 6 is the mass spectrum of trithioacetaldehyde produced according to the synthesis set forth in Example IV.
Figure 7:
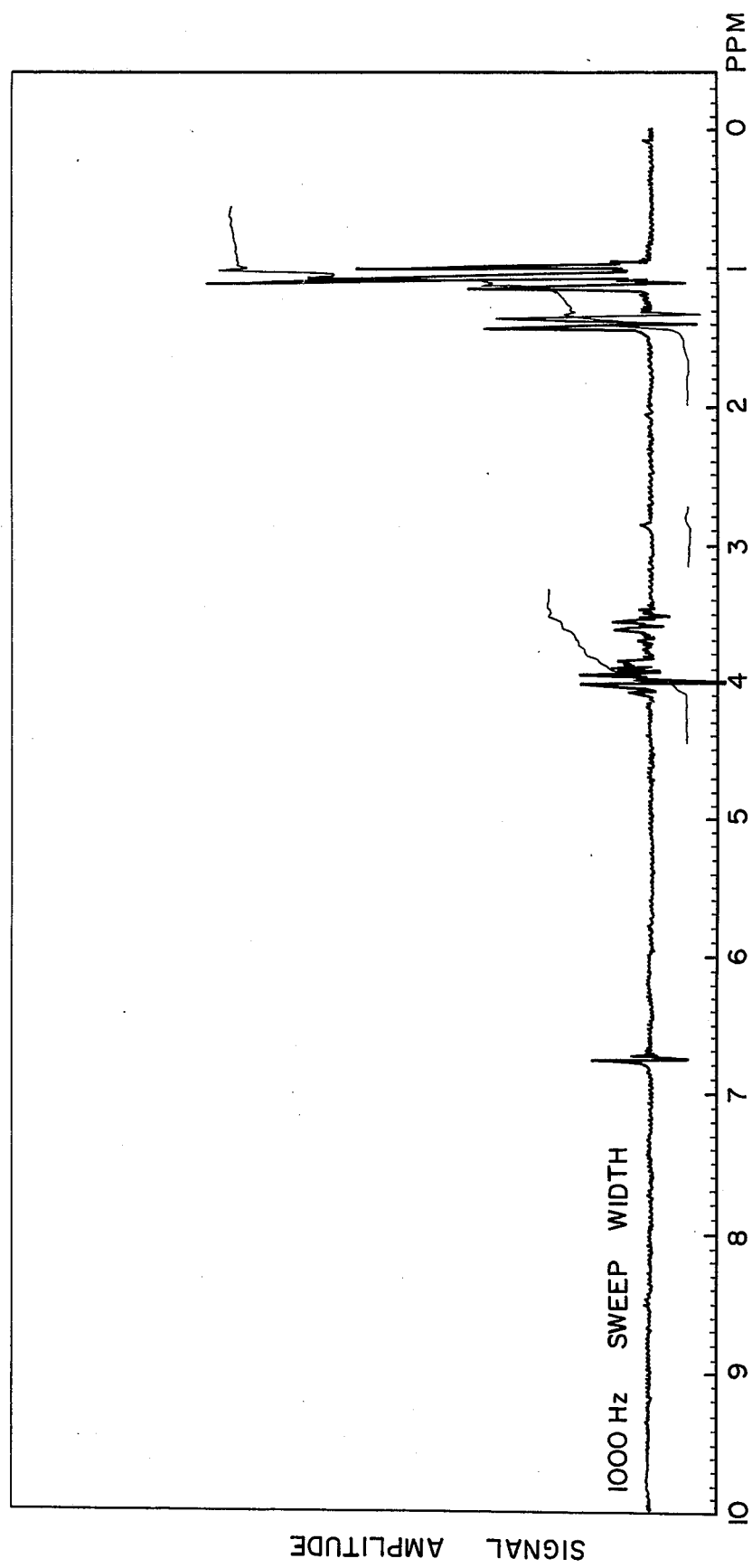
FIG. 7 is the NMR spectrum of trithioacetaldehyde ("α" and "β" forms) produced according to the synthesis set forth in Example IV.

FIG. 6 is the mass spectrum of synthetic trithioacetaldehyde. FIG. 7 is the NMR spectrum of synthetic trithioacetaldehyde ("alpha" and "beta" forms).

EXAMPLE V

The following formulations are produced:

| Formulation A | | |
|---|---|---|
| 1.9 | gm | Natural black currant juice, concentrate |
| 0.1 | gm | Natural black current esters |
| 10.0 | ml | Sugar Syrup 32°Be |
| q.s. | 100 ml | Spring Water |
| Formulation B | | |
| 1.9 | gm | Natural Black currant juice, concentrate |
| 0.1 | gm | Buchu leaf oil 0.1% (ethanol 95%) |
| 10.0 | ml | Sugar Syrup 32°Be |
| q.s. | 100 ml | Spring water |
| Formulation C | | |
| 1.9 | gm | Natural black currant juice, concentrate |
| 0.1 | gm | Niribine* 10% (ethanol 95%) |
| 10.0 | ml | Sugar Syrup 32°Be |
| q.s. | 100 ml | Spring water |

*Niribine is produced by distilling an alcoholic macerate of black current buds.

| Formulation D | | |
|---|---|---|
| 1.9 | gm | Natural black currant juice, concentrate |
| 0.1 | gm | 2,2,4,4,6,6,-hexamethyl-s-trithiane 0.1% (ethanol 95%) |
| 10.0 | ml | Sugar Syrup 32°Be |
| q.s. | 100 ml | Spring water |
| Formulation E | | |
| 1.9 | gm | Natural black currant juice, concentrate |
| 1.9 | gm | Natural black currant juice, concentrate |
| 0.1 | gm | 2,2,4,4,6,6,-hexamethyl-s-trithiane 0.1% (ethanol 95%) |
| 10.0 | ml | Sugar Syrup 32°Be |
| q.s. | 100 ml | Spring water |
| Formulation F | | |

-continued

| 1.9 | gm | Natural black currant juice, concentrate |
| 10.0 | ml | Sugar Syrup 32°Be |
| q.s. | 100 ml | Spring water |

Each of the above-mentioned formulations is compared with one another by a panel composed of 10 tasters. Formulation F is generally considered by the panel to be flat and not very characteristic for fresh black currant. Formulations B, C, D and E are considered as having substantially fresh and more pleasant notes than formulation F. In summary, formulations D and E were preferred as the best black currant juice formulations. In conclusion, for use in black currant flavor, the material 2,2,4,4,6,6-hexamethyl-s-trithiane can be used at rates of one-tenth of that of Buchu leaf oil in black currant juice.

It is further to be concluded that 2,2,4,4,6,6-hexamethyl-s-trithiane can successfully replace Buchu leaf oil, Niribine and/or natural black currant esters wherever the ingredient is used in reinforced black currant juices, substituted black currant juices and imitation black currant flavors.

EXAMPLE VI

Basic Black Currant Formulation

Trithioacetone has been added to a basic black currant flavor formulation at the rate of 1.5%. Both flavors have been compared in water at the rate of 200 ppm and evaluated by a bench panel. The flavor containing trithioacetone has had the characteristic aroma and taste of ripe black currants or fresh black currant juice. This typical note was not present in the basic black currant formulation. Therefore all members of the panel preferred the flavor containing trithioacetone. Detailed below is the Basic Black Currant Formulation to which is added trithioacetone at the rate of 1.5%.

| Ingredient | Parts by Weight |
| --- | --- |
| cis-3-hexen-1-ol | 5 |
| alpha-phellandrene | 1.5 |
| terpinenol-4 10% in ethyl alcohol | 3 |
| para-hydroxy benzyl acetone | .5 |
| vanillin | 2 |
| ethyl maltol | .6 |
| methyl benzoate | .2 |
| benzaldehyde | 2 |
| benzylpropionate | 4 |
| isobutylacetate | 5 |
| coriander oil | 0.5 |
| ethylbutyrate | 8 |
| dimethylsulfide | 3 |
| fusel oil | 8 |
| acetic acid | 10 |
| alpha-ionone 10% | 0.5 |
| ethyl heptanoate | 0.5 |
| propylene glycol | 934 |
|  | 1000 |

EXAMPLE VII

A. 120 Grams of the flavor composition of Example VI is emulsified in a solution containing 300 gm gum acacia and 700 gm water. The emulsion is spray-dried with a Bowen Lab Model Drier utilizing 250 c.f.m. of air with an inlet temperature of 500°F, and outlet temperature of 200°F., and a wheel speed of 50,000 r.p.m.

B. The following mixture is prepared:

| Ingredient | Parts by Weight |
| --- | --- |
| Liquid flavor composition of Example VII | 25 |
| Propylene glycol | 1 |
| Cab-O-Sil M-5 (Brand of Silica produced by the Cabot Corporation of 125 High Street, Boston, Mass. 02110; Physical Properties: Surface Area: 200 m²/gm Nominal Particle Size: 0.012 mccrons Density: 2.3 lbs./cu.ft.) | 3 |
| Ethyl cellulose | 8 |

The Cab-O-Sil and ethyl cellulose is dispersed in the liquid flavor composition of Example VI with vigorous stirring, thereby resulting in a viscous liquid. 65 Parts by weight of the powder flavor composition of Part A is then blended into said viscous liquid, with stirring at 25°C for a period of 30 minutes resulting in a dry, free flowing sustained release flavor powder.

EXAMPLE VIII

Chewing Gum 100 parts by weight of chicle are mixed with 4 parts by weight of the flavor prepared in accordance with Example VII. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting black currant flavor.

EXAMPLE IX

Chewable Vitamin Tablets

The flavor material produced according to Example VIII is added to a Chewable Vitamin Tablet Formulation at a rate of 5 gm/Kg which Chewable Vitamin Tablet Formulation is prepared as follows:

In a Hobart Mixer, the following materials are blended to homogeneity:

|  | Gms/1000 Tablets |
| --- | --- |
| Vitamin C (ascorbic acid) as ascorbic acid-sodium ascorbate mixture 1:1 | 70.0 |
| Vitamin B₁ (thiamine mononitrate) as Rocoat thiamine mononitrate 33 1/3% (Hoffman La Roche) | 4.0 |
| Vitamin B₂ (riboflavin) as Rocoat riboflavin 33 1/3% | 5.0 |
| Vitamin B₆ (pyridoxine hydrochloride) as Rocoat pyridoxine hydrochloride 33 1/3% | 4.0 |
| Niacinamide asRocoatniacinamide 33 1/3% | 33.0 |
| Calcium pantothenate | 11.5 |

-continued
Gms/1000 Tablets

| | |
|---|---|
| Vitamin B$_{12}$ (cyanocobalamin) as Merck 0.1% in gelatin | 3.5 |
| Vitamin E (dl-alpha tocopheryl acetate) as dry Vitamin E acetate 33 1/3% Roche | 6.6 |
| d-Biotin | 0.044 |
| Certified lake color | 5.0 |
| Flavor Example VII | 2.5 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong black currant flavor for a period of 12 minutes.

EXAMPLE X 0.5% trithioacetone is added to a commercial quality of grapefruit oil. The oils with and without this chemical are compared in water at the rate of 10 ppm. The aroma and taste characteristics of the modified oil is considered as much more characteristic of grapefruit peel than of the oil without this chemical. Therefore, a bench panel unanimously prefers the oil containing trithioacetone.

EXAMPLE XI

A. A 40% dextrin solution is freeze-dried. This is accomplished by a conventional technique such as that described in column 4 of U.S. Pat. No. 3,404,007. The freeze-dried material is then milled to a particle size of 20–40 mesh.

100 Grams of this freeze-dried material are then combined with 50 grams of the flavored grapefruit oil (containing trithioacetone) of Example X. This is accomplished by mixing the materials in a suitable blender, such as a ribbon blender. This results in a dry, free-flowing powder having the advantages heretofore described. To ensure against atmospheric reaction or vaporization of the orange oil in the solid matrix, the powder is given a protective coating to seal the entrances to the interstices or cavities in the porous particulate matrix. One suitable form of coating is a dextrin solution which has the property of forming an impermeable film for preventing the escape of permeation of the flavoring oil.

B. The following mixture is prepared:

| Ingredient | Parts by Weight |
|---|---|
| Liquid flavor composition of Example X (containing trithioacetone) | 52 |
| Propylene glycol | 1 |
| Cab-O-Sil M-5 (Brand of Silica produced by the Cabot Corporation of 125 High Street, Boston, Mass. 02110; Physical Properties: Surface Area: 200 m²/gm Nominal Particle Size: 0.012 microns Density: 2.3 lbs./cu.ft.) | 3.8 |
| Ethyl cellulose | 2.2 |

The Cab-O-Sil and ethyl cellulose is dispersed in the liquid flavor composition of Example X with vigorous stirring, thereby resulting in a viscous liquid. 44 Parts by weight of the powder flavor composition of Part A is then blended into the said viscous liquid, with stirring at 25°C for a period of 30 minutes resulting in a thixotropic sustained release flavor paste.

EXAMPLE XII

Chewing Gum 100 parts by weight of chicle are mixed with 4 parts by weight of the flavor prepared in accordance with Example XI. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting grapefruit flavor.

EXAMPLE XIII

Chewable Vitamin Tablets

The flavor material produced according to the process of Example XII is added to a Chewable Vitamin Tablet Formulation at a rate of 6 gm/Kg which Chewable Vitamin Tablet Formulation is prepared as follows:

In a Hobart Mixer, the following materials are blended to homogeneity:

| | Gms/1000 Tablets |
|---|---|
| Vitamin C (ascorbic acid) as ascorbic acid-sodium ascorbate mixture 1:1 | 70.0 |
| Vitamin B$_1$ (thiamine mononitrate) as Rocoat thiamine mononitrate 33 1/3 (Hoffman La Roche) | 4.0 |
| Vitamin B$_2$ (riboflavin) Rocoat riboflavin 33 1/3% | 5.0 |
| Vitamin B$_6$ (pyridoxine hydrochloride) as Rocoat pyridoxine hydrochloride 33 1/3% | 4.0 |
| Niacinamide as Rocoat niacinamide 33 1/3% | 33.0 |
| Calcium pantothenate | 11.5 |

-continued

Gms/1000 Tablets

| | |
|---|---|
| Vitamin B₁₂ (cyanocobalamin) as Merck 0.1% in gelatin | 3.5 |
| Vitamin E (dl-alpha tocopheryl acetate) as dry Vitamin E acetate 33 1/3% Roche | 6.6 |
| d-Biotin | 0.044 |
| Certified lake color | 5.0 |
| Flavor Example XI | 3.0 |
| Sweetner - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong grapefruit flavor for a period of 12 minutes.

EXAMPLE XIV

The following formulations are produced:

Formulation A

| | | |
|---|---|---|
| 1.9 | gm | Natural black currant juice, concentrate |
| 0.1 | gm | Natural black currant esters |
| 10.0 | ml | Sugar Syrup 32°Be |
| q.s. | 100 ml | Spring water |

Formulation B

| | | |
|---|---|---|
| 1.9 | gm | Natural black currant juice, concentrate |
| 0.1 | gm | Buchu leaf oil 0.1% (ethanol 95%) |
| 10.0 | ml | Sugar Syrup 32°Be |
| q.s. | 100 ml | Spring water |

Formulation C

| | | |
|---|---|---|
| 1.9 | gm | Natural black currant juice, concentrate |
| 0.1 | gm | Niribine* 10% (ethanol 95%) |
| 10.0 | ml | Sugar Syrup 32°Be |
| q.s. | 100 ml | Spring water |

*Niribine is produced by distilling an alcoholic macerate of black current buds.

Formulation D

| | | |
|---|---|---|
| 1.9 | gm | Natural black currant juice, concentrate |
| 0.1 | gm | 2,4,6-trimethyl-s-trithiane (ethanol 95%) |
| 10.0 | ml | Sugar Syrup 32°Be |
| q.s. | 100 ml | Spring water |

Formulation E

| | | |
|---|---|---|
| 1.9 | gm | Natural black currant juice, concentrate |
| 0.1 | gm | 2,4,6-trimethyl-s-trithiane (ethanol 95%) |
| 10.0 | ml | Sugar Syrup 32°Be |
| q.s. | 100 ml | Spring water |

Formulation F

| | | |
|---|---|---|
| 1.9 | gm | Natural black currant juice, concentrate |
| 10.0 | ml | Sugar Syrup 32°Be |
| q.s. | 100 ml | Spring water |

Each of the above-mentioned formulations is compared with one another by a panel composed of 10 tasters. Formulation F is generally considered by the panel to be flat and not very characteristic for fresh black currant. Formulations B, C, D and E are considered as having substantially fresh and more pleasant notes than formulation F. In summary, formulations D and E were preferred as the best black currant juice formulations. In conclusion, for use in black currant flavor, the material 2,4,6-trimethyl-s-trithiane can be used at rates of one-tenth of that of Buchu leaf oil in black currant juice.

It is further to be concluded that 2,4,6-trimethyl-s-trithiane can successfully replace Buchu leaf oil, Niribine and/or natural black currant esters wherever the ingredient is used in reinforced black currant juices, substituted black currant juices and imitation black currant flavors.

What is claimed is:

1. A process of altering, modifying or enhancing the fruit flavor or aroma of a foodstuff having a gooseberry, black currant, grape or raspberry taste which comprises adding thereto from about 0.02 up to 100 part per million by weight of a substantially pure form of 2,2,4,4,6,6-hexamethyl-S-trithiane.

2. A process for altering, modifying or enhancing the black currant flavor or aroma of a foodstuff having a black currant taste which comprises adding thereto from about 0.02 up to 100 parts per million by weight of a substantially pure form of 2,2,4,4,6,6-hexamethyl-S-trithiane.

3. A food flavor composition useful in altering, modifying or enhancing the black currant taste of a foodstuff consisting essentially of from 0.1 up to 90% by weight of a substantially pure form of 2,2,4,4,6,6-hexamethyl-S-trithiane, the remainder of said composition being a black currant juice concentrate.

* * * * *